(12) United States Patent
Mura (10) Patent No.: US 7,726,814 B2
(45) Date of Patent: Jun. 1, 2010

(54) REFLECTION MICROSCOPE AND METHOD

(75) Inventor: Sergio Mura, Florence (IT)

(73) Assignee: Costruzioni Strumenti Oftalmici S.r.l., Florence (IT)

(*) Notice: Subject to any disclaimer, the term of this patent is extended or adjusted under 35 U.S.C. 154(b) by 430 days.

(21) Appl. No.: 11/632,084

(22) PCT Filed: Jul. 6, 2005

(86) PCT No.: PCT/IB2005/001908

§ 371 (c)(1),
(2), (4) Date: Jan. 8, 2007

(87) PCT Pub. No.: WO2006/006048

PCT Pub. Date: Jan. 19, 2006

(65) Prior Publication Data

US 2007/0263172 A1 Nov. 15, 2007

(30) Foreign Application Priority Data

Jul. 8, 2004 (EP) .................................. 04425498

(51) Int. Cl.
*A61B 3/14* (2006.01)
*A61B 3/10* (2006.01)
*G02B 21/00* (2006.01)

(52) U.S. Cl. ..................... 351/206; 351/221; 359/368

(58) Field of Classification Search ......... 351/205–206, 351/208, 210–211, 214, 221, 200, 213; 359/629, 359/640, 368, 381, 618, 625, 636–639, 372, 359/389

See application file for complete search history.

(56) References Cited

U.S. PATENT DOCUMENTS

| 5,381,194 | A |   | 1/1995  | Nishio et al.   | 351/208 |
| 5,471,261 | A | * | 11/1995 | Yoshizo et al.  | 351/210 |
| 5,757,461 | A | * | 5/1998  | Kasahara et al. | 351/206 |
| 6,164,778 | A |   | 12/2000 | Takagi et al.   | 351/206 |

FOREIGN PATENT DOCUMENTS

| EP | 0628281 A1    | 12/1994 |
| EP | 0641541 A1    | 3/1995  |
| WO | WO 03015623 A2 | 2/2003 |
| WO | WO 03015623 A3 | 2/2003 |

* cited by examiner

*Primary Examiner*—Scott J Sugarman
*Assistant Examiner*—Dawayne A Pinkney
(74) *Attorney, Agent, or Firm*—Pollack, P.C.

(57) ABSTRACT

An apparatus and a method for operating an endothelium reflection microscope. The apparatus includes an optical head, which comprises: (i) an illuminating system, (ii) a frontal eye observation optical system along a central channel in which an alignment-use light spot is received and imaged by a camera having a digital optical sensor, and (iii) an enlarged-imaging optical system for enlarged observation or photographing of the subject part by the digital camera. The apparatus further comprises a motor for operating the optical head, and a CPU controller for automatically controlling the motor, the illuminating system and the frontal eye observation optical system. The method comprises an endothelium image acquisition procedure in which the grey level inside a check area of the camera sensor is checked constantly during advancement along the Z-axis; when the grey level reaches a predetermined threshold value, a delay time ($\Delta t$) is triggered; and when the delay time ($\Delta t$) lapses, acquisition by the digital camera of one or more images of the endothelium is enabled.

11 Claims, 8 Drawing Sheets

REFLECTION MICROSCOPE AND METHOD

FIELD OF THE INVENTION

The present invention relates generally to microscopes and, more particularly, to non-contact endothelium microscopes and the like.

BACKGROUND OF THE INVENTION

The endothelium is the innermost layer of tissues forming the cornea, consisting of a single layer of flat polygonal cells. One purpose of the endothelium is to control water content and, thus, permit suitable hydration of the cornea. Accordingly, the shape and number of cells in the endothelium influence the quality of one's vision. As the transparency of the cornea depends on a rather delicate balance of factors, there are a number of diseases that can readily disrupt this balance, cause a loss of transparency, and, thereby, hinder the quality of vision.

Endothelium cells in children and young people are typically hexagonal in shape These cells, however, do not reproduce themselves. At birth, the density of endothelium cells is about 4000 per square millimeter but, as the years pass, the cells begin to change in shape, and the total number of cells decreases. In an adult, the average density is about 2700 cells per square millimeter, with a range of about 1600 to about 3200 cells per square millimeter. The loss of endothelium cells with age is accompanied by two main morphological changes: (i) the presence of cells with different surface areas, and (ii) an increase in the number of cells that are shaped differently from their original hexagonal shape.

Evaluation of the corneal endothelium has been found useful for providing a first clinical indication as to the potential risks of surgery, and for verifying a diagnosis or the effectiveness of a particular therapy. In these evaluations, it is considered particularly important to observe heterogeneous portions of the endothelium, such as intracellular and intercellular areas of no reflectance (dark spots), hyper reflective areas (bright spots), empty areas in the cells layer (guttae), bubbles, as well as Descemet's membrane rupture lines.

Such portions of the endothelium can be checked relative to the evolution of the various diseases of the endothelium which are of an inflammatory or dystrophic nature. Quantitative evaluation involves the assignment of a numeric parameter to a selected photographic field, which parameter is used to study variations in the endothelium over time, or for comparison between different patients.

The most readily accessible parameter is the average cellular density, obtained for comparison purposes by counting the number of cellular elements. A first evaluation method, in this regard, is accomplished by comparing the cellular dimensions with those of the hexagonal reticules that correspond to determined densities. According to a second method, counting of the number of cellular elements is, instead, performed by using fixed or variable reticules.

While beneficial, neither method provides information as to the evolution of the cellular dimensions. Such information can be obtained, however, by identifying, in addition to the dimension of the average cellular area and its variability, the perimeters of the cellus as well. This information is obtained through observation using an endothelium reflection microscope, which was first introduced in opthalmologic practice in 1960 by David Maurice who, by modifying a metallography microscope, obtained photographic images of a rabbit's corneal endothelium. Using the same principles, a microscope was developed subsequently that was able to photograph the endothelium without contacting the eye.

Generally speaking, reflection microscopes of the non-contact type are derived from high magnification microscopes with normal slit lamps. These microscopes are based on the principle of visualization of a selected structure in relation to its ability to reflect an incident ray of light used for illumination. In the most commonly used technique (i.e., triangulation), the observation angle is about 45°, the microscope being oriented such that the bisecting axis of the angle of view is perpendicular to the plane tangential to the corneal surface.

Non-contact endothelium microscopy is particularly suitable for applications where contact with the cornea can be dangerous, such as immediately after surgery or in cases where the structure of the cornea is extremely fragile. By integrating the microscope with techniques of image analysis, the apparatus also provides a quantitative description of endothelium tissue, in the form of average cellular density and specific morphometric parameters.

In one conventional arrangement, a non-contact endothelium microscope apparatus is provided, which includes an optical unit with an illuminating system, for obliquely illuminating through a slit a surface portion of a patient's eyeball, and frontal eye observation, optical system, wherein an alignment-use indicator light for positional adjustment of the imaging optical axis is projected toward the patient's eye and the resulting reflected light is received and imaged by a TV camera. An enlarged-imaging optical system is also provided for enlarged observation or enlarged photographing, of the subject surface portion on the TV camera based on slit illuminating light from which the eyeball surface has been illuminated.

In addition, a photo-detector is arranged so as to detect a position at which the enlarged-imaging optical system has been focused on the subject surface portion, via a reflected optical path other than that through which the enlarged image has been formed by the enlarged-imaging optical system. The optical unit is automatically moved, in response to the location of the indicator light displayed on a video monitor, both in a transverse direction and toward the eye, so that the location "chases" a specified position on the screen. In this manner, when the photo-detector detects focusing, the enlarged visual image of the subject portion of the cornea is photographed via the TV camera.

The same numerals are used throughout the drawing figures to designate similar elements. Still other objects and advantages of the present invention will become apparent from the following description of the preferred embodiments.

While this system has been found workable, placement of a focusing detection, photo-detector along a supplementary reflected optical path, renders the apparatus complicated, and thus costly for providing and maintaining reliable results.

OBJECTS AND SUMMARY OF THE INVENTION

Accordingly, it is an object of the present invention to provide testing of the endothelium without the use of sensors, photosensors or placement of other devices in a reflected optical path.

Another object of the present invention is to provide an apparatus that achieves a higher quality endothelium image than those of conventional arrangements while reducing or eliminating the need for electronic components, thereby providing greater reliability, completeness and flexibility of use.

In accordance with one aspect of the present invention, there is provided a method for operating an endothelium reflection microscope apparatus. The apparatus includes an optical head which comprises: an illuminating system, for obliquely illuminating, along a side projection axis through a slit, an eyeball surface of a patient's eye; an eye-front observation optical system along a central channel in which alignment-use indicator light for positional adjustment of the imaging optical center is projected toward the eye and the resulting reflected light spot is received and imaged by a camera comprising a digital optical sensor; and an enlarged-imaging optical system arranged along a side reflection axis for enlarged observation or photographing of the subject part by the digital camera based on slit illuminating light with which the eyeball surface has been illuminated. The apparatus further comprises a drive for moving the optical head along three Cartesian directions comprising an advancement direction (Z-) generally parallel to the central channel and transverse alignment directions (X-, Y-), and a CPU controller for automatically controlling the drive, the illuminating system, and the eye-front optical system.

The method includes an alignment procedure in which the optical head is moved along the alignment directions (X-, Y-) so that the reflected light spot and the camera optical sensor are mutually centered, and an endothelium image acquisition procedure in which the optical head is moved along the advancement direction (Z-). The image acquisition procedure comprises the steps of:

(i) constantly checking the grey level inside a check area of the camera sensor, during its progression along the advancement direction (Z-), the check area being displaced generally toward a border of the sensor corresponding to the entry side of reflection of the slit light, shifting in response to movement of the optical head in the advancement direction (Z-);

(ii) when the grey level reaches a predetermined threshold value, triggering a delay time ($\Delta t$); and (iii) when the delay time ($\Delta t$) lapses, enabling acquisition of one or more images of the endothelium by the digital camera.

BRIEF DESCRIPTION OF THE DRAWINGS

A specific, illustrative apparatus for morphometric analysis of the corneal endothelium by direct image acquisition, according to the present invention, is described below with reference to the accompanying drawings, in which.

DETAILED DESCRIPTION OF THE PREFERRED EMBODIMENTS

Referring now to the drawings and, more particularly, to FIGS. 1-9, there is shown generally a specific, illustrative apparatus for examination of the corneal endothelium and a method of operating the same, according to various aspects of the present invention. According to one embodiment, the apparatus comprises a movable optical head or microscope 1 having a CCD high speed camera 2, e.g., a monochrome digital camera with shooting capacity of at least one hundred frames per second with FireWire high speed data output, such as an IEEE 1394 port or equivalent.

Figure 3:
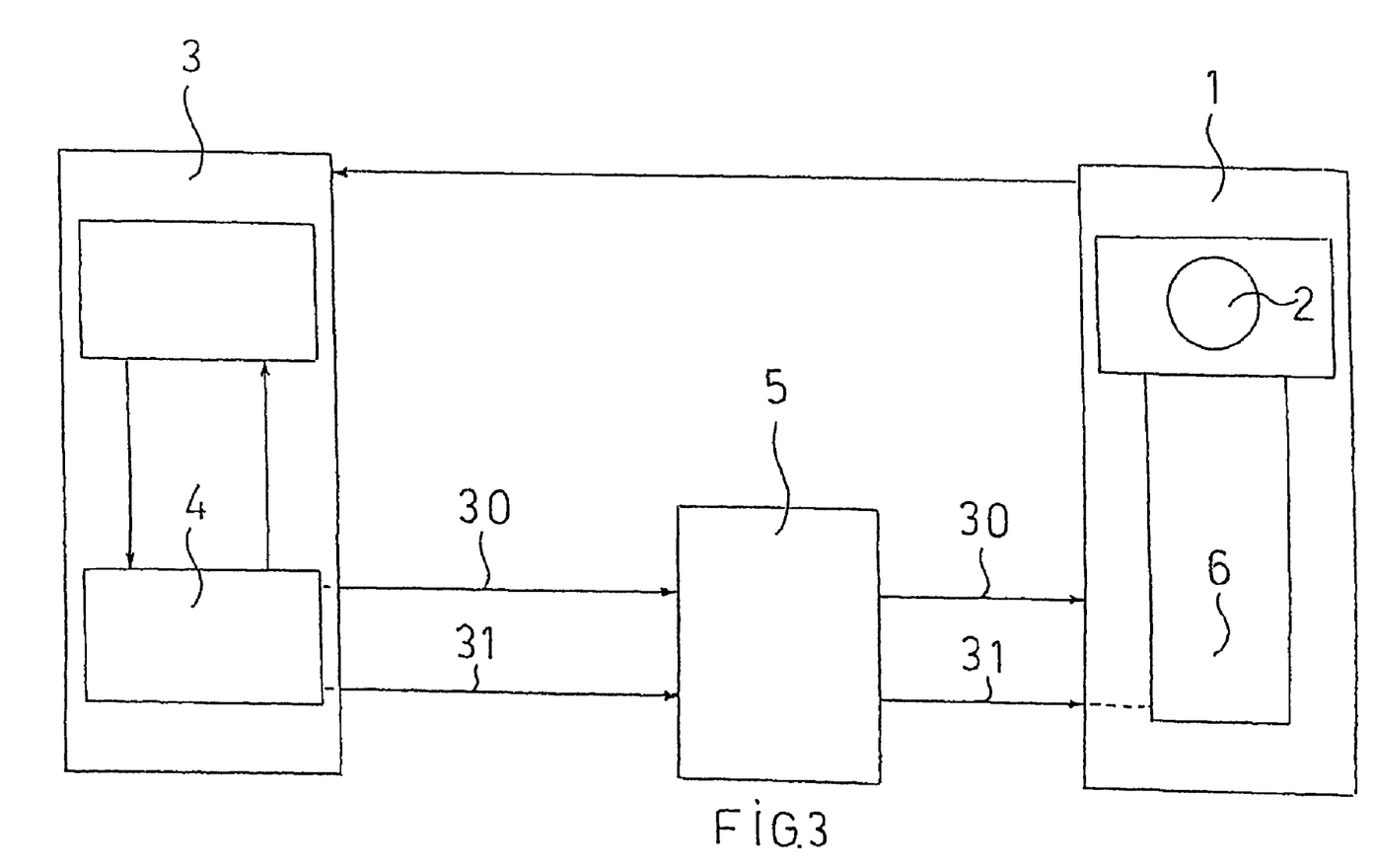
FIG. 3 illustrates schematically a hardware configuration of an apparatus according to one aspect of the present invention.

High speed camera 2 is connected directly to a central processing unit (CPU) 3. The CPU includes a controller 4, e.g., a 65XX type controller produced by National Instruments Corporation (Austin, Tex., U.S.A.) or equivalent. Controller 4 operates a power driver board 5, such that the signal coming from the CPU is sufficient to power electric DC motors 6, as described in more detail below.

One purpose of the motors is to position microscope 1 and the associated camera 2, upon their automatic control by CPU 3, so that center portion 7 of the eye to be examined may readily be found. This is accomplished by reflecting light from an infrared, light emitting diode (LED) 8 into the corneal surface, the LED being mounted to the mobile head of the apparatus, which comprises optical head or microscope 1 and camera 2.

Figure 1:
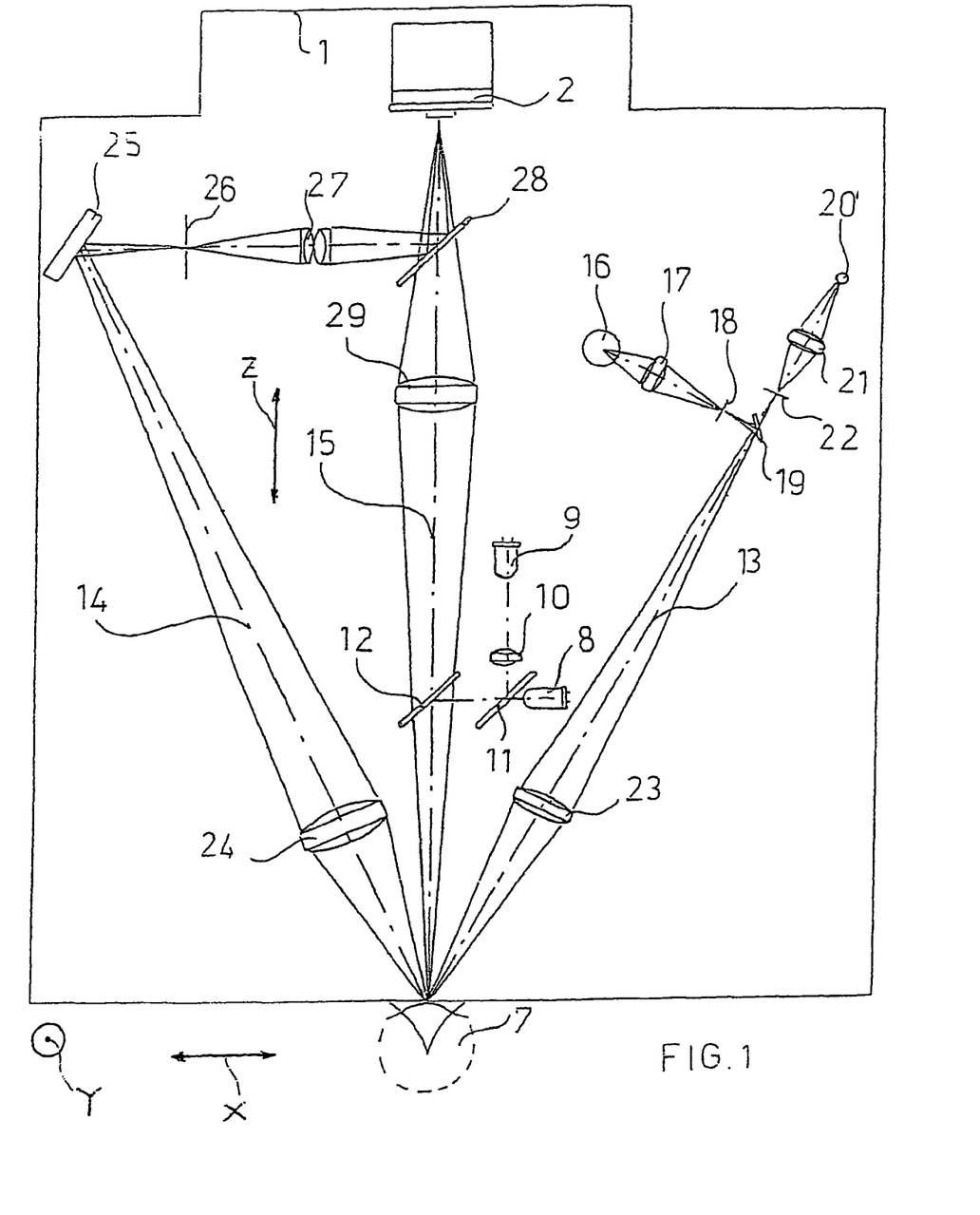
FIG. 1 shows schematically an optical pathway according to a first embodiment of the present invention.

The aforementioned electronic components are preferably connected one another according to known arrangement. Alternatively, as shown in FIG. 1, an optical scheme may be used wherein a second LED 9 with associated optics 10 is arranged in proximity to infrared LED 8 in order to provide a fixation point in association with a semireflecting mirror 11 and a semireflecting mirror 12, as necessary, to center the patient's eye relative to the microscope and obtain the triangulation necessary to conduct the test. These components, like those forming the optical scheme, are triangulation elements for the endothelium test, as are known and already in use for such applications.

In accordance with one aspect of the present invention, the optical scheme comprises a side projection axis 13, a side reflection axis 14 and a central channel 15. In the embodiment of FIG. 1, a halogen lamp 16 is arranged, transversely to side projection axis 13, with a lamp condenser 17 and a slit 18. Along the side projection axis, a semireflecting mirror 19 is also positioned for receiving the light beam generated by the halogen lamp, a beam that can be generated by a halogen lamp, and the beam of light that can be generated by a photoflash or photoflash lamp 20 located at the beginning of side projection axis 13. On the same axis, following the photoflash lamp 20 is a photoflash condenser 21, a slit 22 and, beyond semireflecting mirror 19, an optical unit 23 that concentrates the beam at center portion 7 of the patient's eye. In the arrangement illustrated in FIG. 2, lamp 16, condenser 17, slit 18, semireflecting mirror 19, and photoflash lamp 20 are replaced with a stroboscopic lamp 36 having the same function as, and activated analogously to, to the previous optical scheme.

Figure 2:
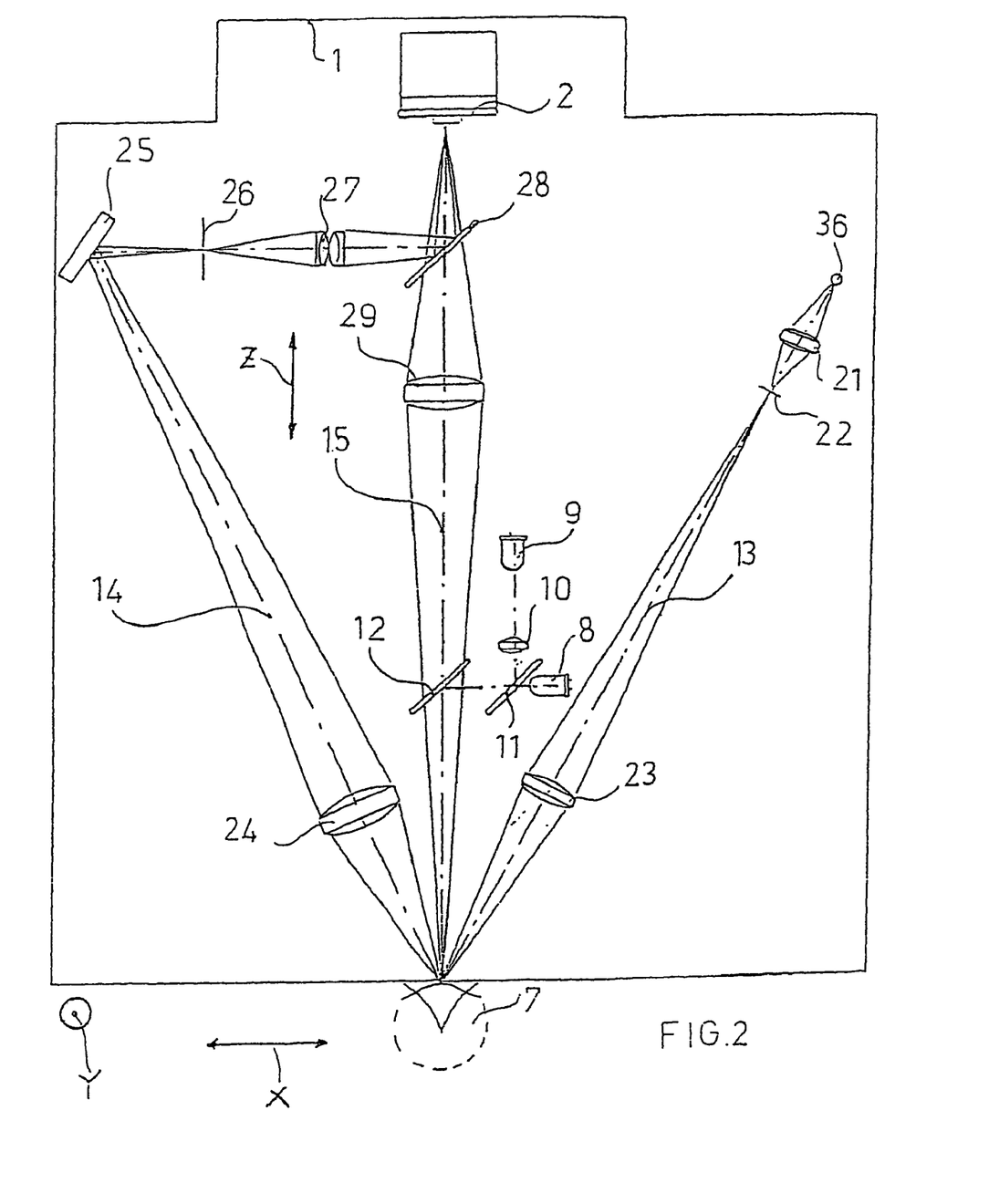
FIG. 2 shows schematically an optical pathway according to a second embodiment of the present invention.

A side reflection optical unit 24, arranged along side reflection axis 14, concentrates the reflected beam and the endothelium image on a mirror 25, from which the beam and image signal are reflected to central channel 15 passing through a filter 26 and a magnifying optical unit 27. The beam, and the endothelium image conveyed thereby, joins the central channel at a point where a dichroic mirror 28 is located.

Starting from the eye to be examined, channel 15 accommodates, in addition, semireflecting mirror 12 and a central optical unit 29 that concentrates the image of the eye and of LED 8 on high speed camera 2, passing through dichroic mirror 28.

The system is preferably controlled by pulses 30, 31 from controller 4. First pulse 30 transmits an on/off signal to LEDs 8 and 9, to the photoflash lamp, and to the halogen lamp, whereas second pulse 31 transmits a signal for operating motors 6.

The optical head or microscope is driven by the motors along three Cartesian directions where a low-high direction corresponds with a Y-axis direction, motion in a direction horizontally approaching and moving away from the patient's eye corresponds to a Z-axis direction, and movement in a transverse sideways direction corresponds to an X-axis direction.

Turning now to FIGS. 4-9, the microscope, according to another aspect of the present invention, operates as follows. Initially, after arranging the optical head at a desired position, the test commences with turning on LED 9, the LED establishing a fixation point for the patient's eye. At the same time, infrared LED 8 is switched on, thereby projecting a spot of light onto the corneal surface via reflecting mirror 12. This spot is detected by camera 2 along central channel 15. Camera 2 then begins to acquire images, with a resolution of at least around 656× around 400 pixels, taken continuously at a frequency of about 100 Hz.

Desirably, data acquisition procedures are carried out with each acquired frame to identify points (pixels) where the grey level is inside a selected predetermined range, so as to eliminate the darker and clearer points of the predetermined range, to identify all the points that belong to the light spot reflected by the cornea, and thus to precisely outline the same spot.

Figure 4:
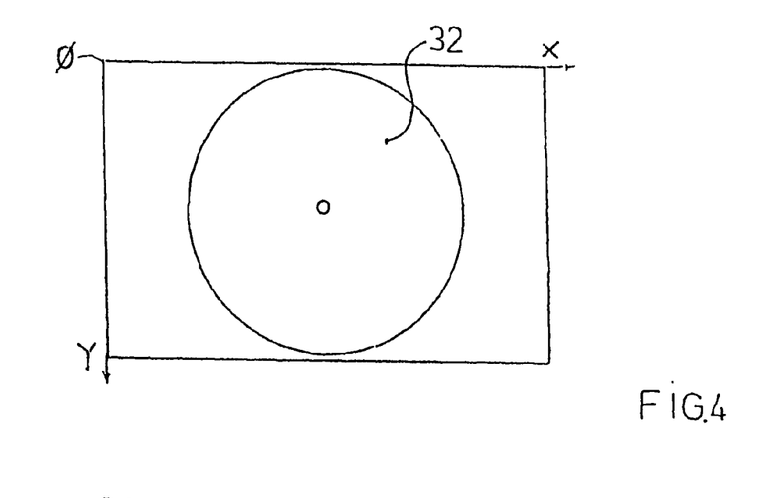
FIG. 4 shows a first image displayed on a monitor screen during image acquisition procedures, according to one aspect of the present invention.

Of all the pixels that form the image of the reflected spot, the X and Y coordinates are calculated, with reference to an upper left angle of the image that coincides with the same position on the camera sensor (See point ø in FIG. 4).

Subsequently, average, variance and standard deviation of the X, Y coordinates are computed so as to define the center of the reflected spot, and to identify the interference of possible remote luminous signals that could be associated mistakenly with the spot.

Driver board 5 is operated continuously so that, through action of electronic motors 6, the luminous spot created by LED 8 follows and coincides with the center of the camera sensor. In practice, the apparatus, according to the present invention, causes the center position 7 of the eye to coincide with the center of the CCD camera sensor and of the video signal processed by the FireWire IEEE 1394 port and the controller, with a feedback control loop for automatic operation of the electric motors.

Figure 5:
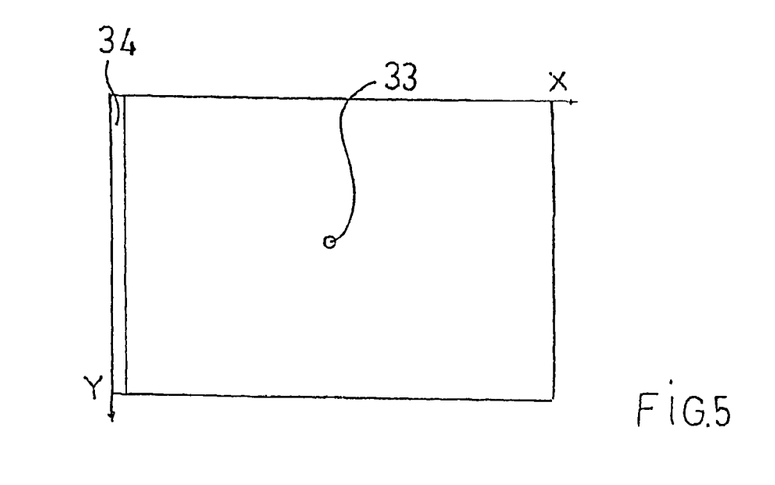
FIG. 5 shows a second image displayed on a monitor screen during image acquisition procedures according to FIG. 4.

More specifically, as illustrated generally in FIGS. 4 and 5, CPU 3 defines two concentric areas, namely, a bigger area 32 and a smaller area 33. The bigger area, simply stated, is the area of the image that is deemed useful for testing purposes, the borders of the image being discarded because they are often affected by undesirable external reflections. When the center of the light spot is outside bigger area 32, further testing is not permitted. Area 32 can be circular in shape, as in the example disclosed, or have a different shape (i.e., be oval, square, etc.)

The radius of area 32 may either be defined by the person operating the apparatus, or established as a design parameter, the center of the area coinciding with the center of the CCD camera sensor. Smaller area 33, on the other hand, is the optimal area for centering, i.e., the target area to be reached by the center of the light spot such that the eye and the camera sensor are centered relative to one another.

In this manner, the center of the reflected spot is calculated, namely, the distance between the spot and the center of small area 33 (which can even be as small as a single pixel). The motors are then operated continuously to drive optical head or microscope 1 along the X and Y directions until such distance is minimized, i.e., until the center of the reflected spot is brought (and kept) within area 33. In practice, the system automatically calculates the center location of the reflected spot relative to the center of area 33 so as to command the motors, accordingly. Through suitable arrangement of driver board 5 and motors 6 in two X-Y directions, movement of the optical head occurs at a frequency equal generally to that with which the frames are taken, i.e., approximately every ten milliseconds.

When the reflected spot (image) is deemed centered at the sensor (See step A in FIGS. 7 and 8), lamp 16 is switched on through a suitable TTL signal that activates the driver board. The lamp illuminates slit 18 through lamp condenser 17, the resulting slit of light projecting on the eye along axis 13 through mirror 19 and lens 23. The optical head is then moved along the Z-axis direction, until triangulation takes place, i.e., until the slit of light, through the geometric conditions that regulate the optical reflection, can be reflected by the corneal surface via reflection axis 14. When reflection occurs, the image projected by the slit is superimposed on the image acquired by camera 2 coming from central channel 15. The aforementioned geometric conditions are such that advancement of the optical head in the Z-axis direction corresponds to a shifting, from left to right (See camera sensor in FIGS. 4 and 5) of the image of the slit reflected by the corneal surface.

To achieve high quality images of the endothelium, it is considered important that the images be captured, and preferably that the cornea be illuminated by photoflash lamp 20, for the duration of time that the incident beam coming from side projection axis 13 is in the optimal position to create the necessary reflection on the layer of endothelium cells. Accordingly, the apparatus, according to one aspect of the present invention, operates as follows.

First, as set forth in FIG. 5, a check area or band 34 is established in a left hand side portion of the image taken by the CCD camera sensor. In the example shown, the check area is a band five pixels wide starting from the left hand border of the sensor, but may be displaced less relative to the center, and be smaller in width and length, depending on the circumstances. Absent triangulation, the image in check area or band 34 is generally comprised of a low intensity, grey background with a low intensity value.

Figure 6:
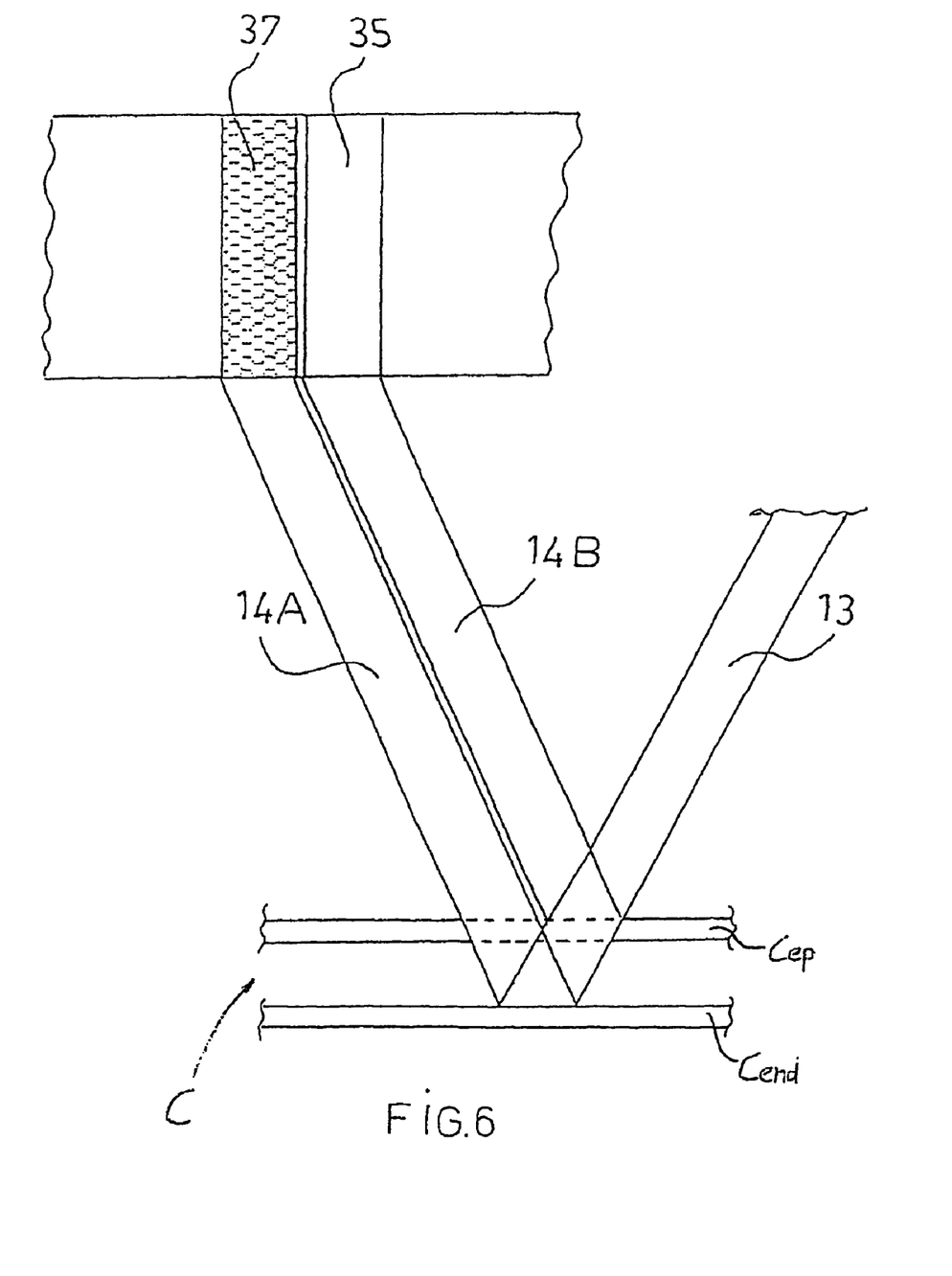
FIG. 6 represents schematically selected reflections obtained using an apparatus according to the present invention.
Figure 7:
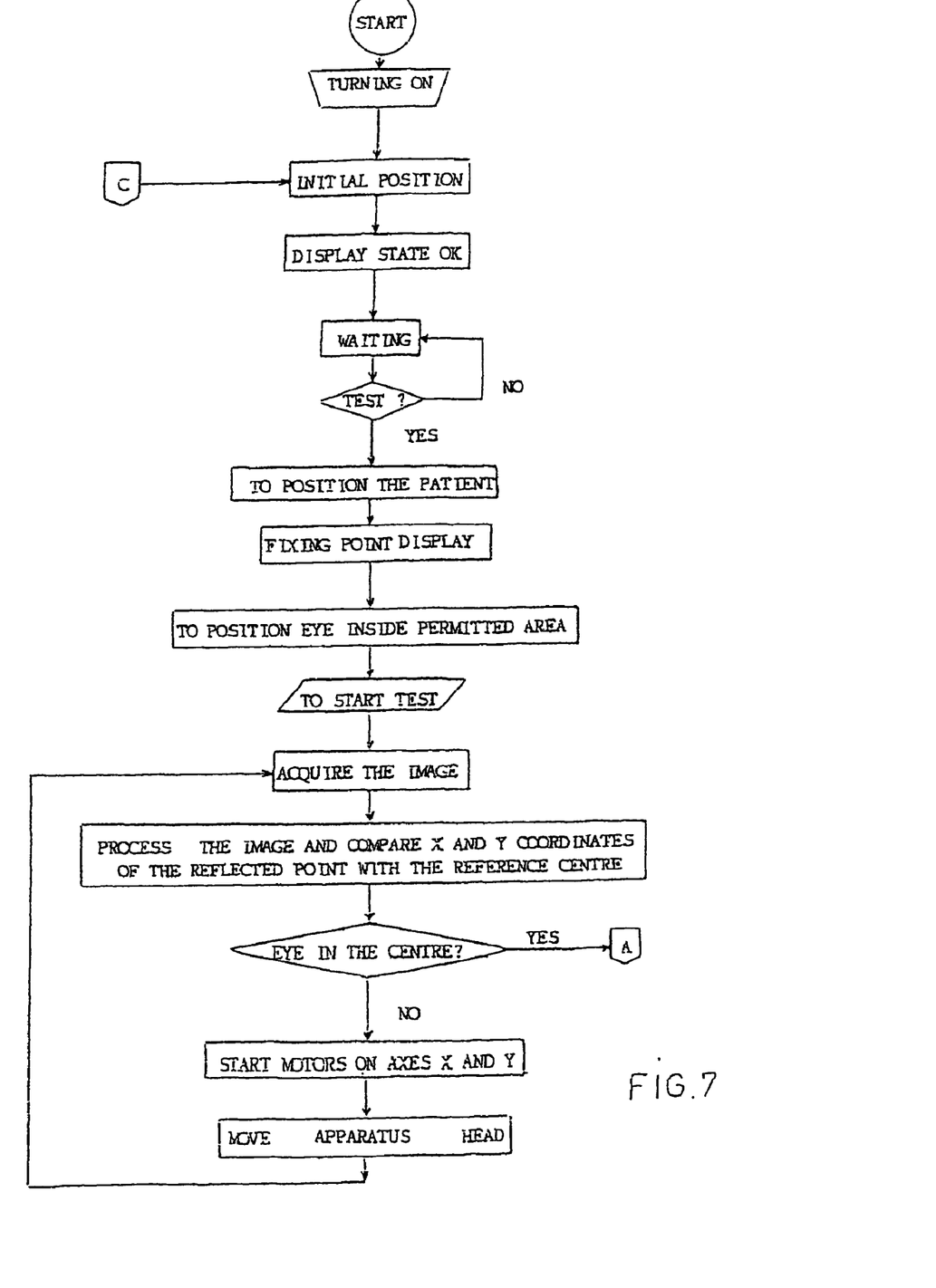
FIG. 7 is a flowchart showing a first procedure for image acquisition using an apparatus, according to one aspect of the present invention.
Figure 8:
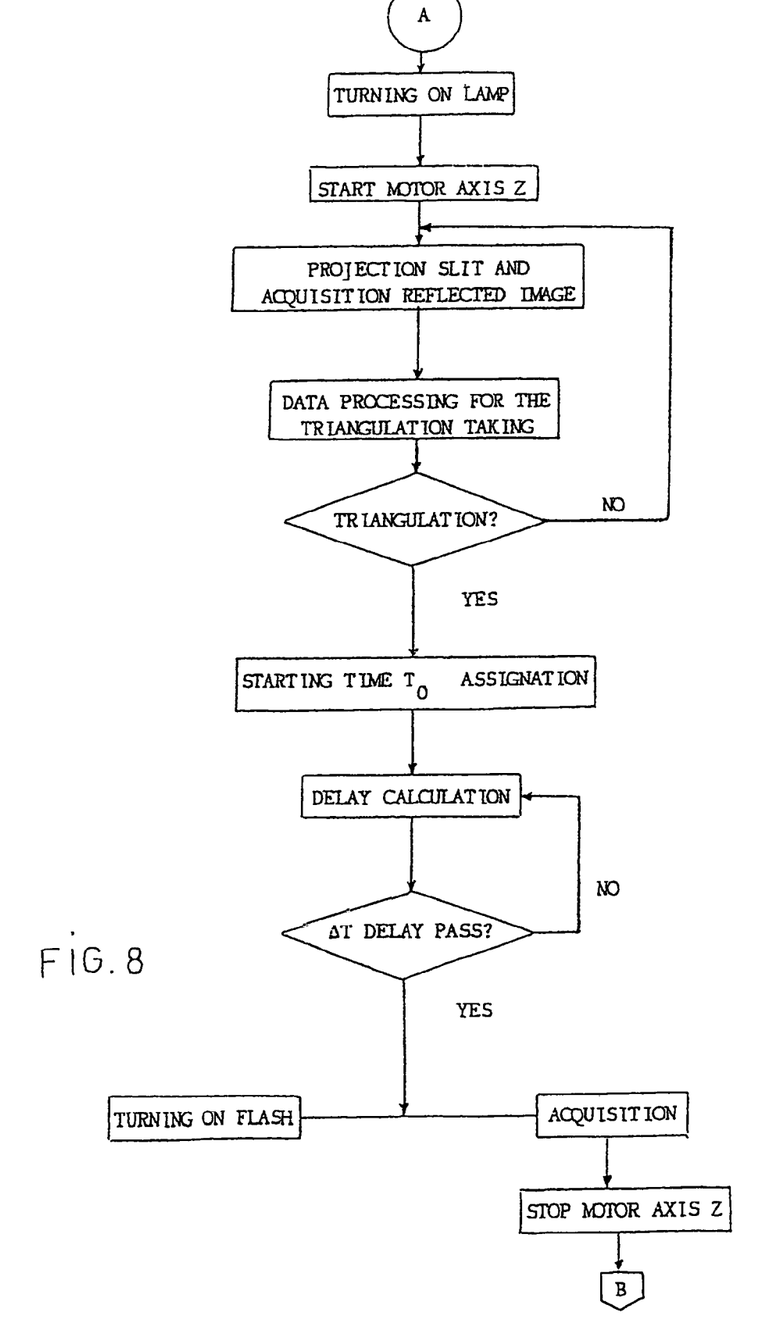
FIG. 8 is a flowchart showing a second procedure for image acquisition using an apparatus according to the present invention.
Figure 9:
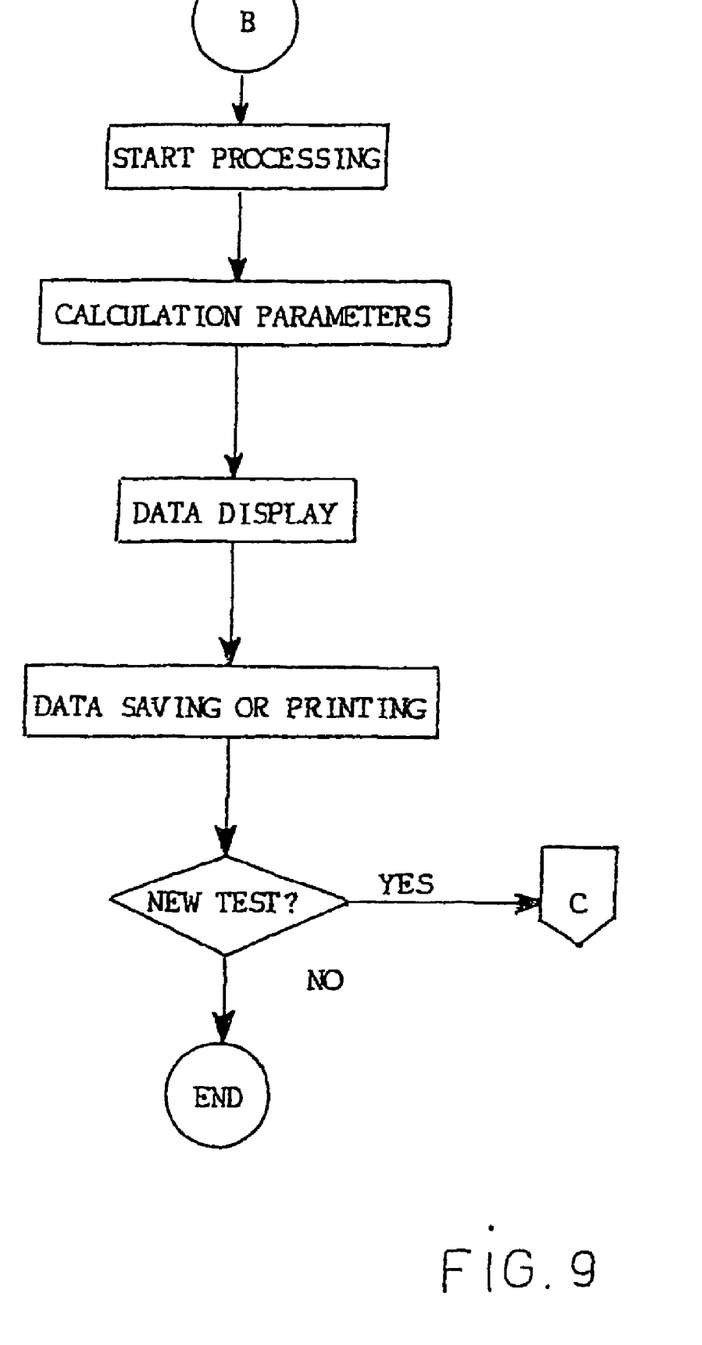
FIG. 9 is a flowchart showing a third procedure for image acquisition using an apparatus according to the present invention.

Check area 34 is checked constantly, during advancement of the optical head in the direction of the Z-axis, against the maximum frequency permitted to be used with the camera (for instance, around 100 frames per second). As best seen in FIG. 6, a beam 14B is reflected by cornea C and, more particularly, by a surface thereof, i.e., the epithelium Cep. Reflected beam 14B is captured by the camera as a luminous strip 35 (i.e., the aforementioned image produced upon illumination of the slit) moving from left to right.

When luminous strip 35 enters the check area, the grey level intensity detected increases to a value greater than a predetermined threshold value; and the corresponding time $t_0$ is fixed or set as a temporal reference. The grey level intensity detected in the check area is accomplished by calculating the average intensity over all the pixels forming the area.

From threshold or reference time $t_0$ a suitable delay time $\Delta t$ is selected to control the acquisition of image data. Indeed, given the velocity of the optical head along the Z-axis and, moreover, the thickness of the cornea, it is only with the selected delay, after image 35 reflected by epithelium Cep has been detected in the check area, that an image reflected by the endothelium arrives at an optimal position for image capture by camera 2. An arrangement of this general description is also shown in FIG. 6, namely, where beam 14A reflected by endothelium Cend produces a strip image 37 displaced rearwardly relative to image 35, as reflected by epithelium Cep.

Generally, the length of time $\Delta t$ between reference $t_0$ and the time when the image of the endothelium is captured is fundamental, and is evaluated based on the advancement speed and the average thickness of the cornea. The delay time $\Delta t$ can, in any case, be adjusted either manually or automatically. Once $\Delta t$ has been reached, photoflash lamp 20 is turned on, thereby illuminating the cornea, and the image of the endothelium is captured by camera 2. A number of different images can be taken, in addition, so that the one of best quality can be chosen. The images are then stored in a database for further processing or treatment. After the data acquisition cycle has ended, the apparatus returns to its starting position and awaits the next test to be performed.

Optionally, both the time delay, $\Delta t$, and position of check area 34 can be varied so as to give to the medical operator the ability to obtain better images, particularly in the case of corneas with specific morphologies. The photoflash lamp, with its supplementary luminous impulse, allows the user to lower the gain of the camera for less "noise" in the images. The photoflash lamp may be actutated upon a selected advance of the optical head relative to the time lapse of $\Delta t$, taking into consideration the lag intrinsic to the device.

Overall, the apparatus, according to the present invention, advantageously provides testing of the endothelium without the use of sensors, photosensors or placement of other devices in a reflected optical path. It also achieves an endothelium image of much higher quality than those of conventional arrangements, while reducing or eliminating the need for electronic components, thereby providing greater reliability, completeness and flexibility of use. The absence of a photosensor or linear sensor along an optical reflection path, and the use of an acquisition procedure, controlled and realized through simple software-based instructions given to the apparatus, results in higher reliability, lower costs and greater flexibility. Furthermore, by allowing the user to capture a number of frames, and then choose the one of highest quality, increases the quality of endothelium images even more, as compared to known arrangements and conventional focusing techniques.

The patients, test data, and captured images are advantageously stored in a database, permitting the medical operator or user to use, review and/or otherwise work on the data collected, even after testing has concluded. In this manner, useful clinical parameters may be readily relied upon and, subsequently, processed so as to determine the number and density of the cells, their shape, their surface, i.e., minimum, maximum and average surface area, their deviation from standard parameters, a variance coefficient, the ratio of cells of various forms, as well as show graphically their distribution, the dimension of cell areas, and their perimeters' distribution.

Moreover, because of the automatic control provided, testing can now be performed with significantly less assistance from the user.

Various modifications and alterations may be appreciated based on a review of this disclosure. These changes and additions are intended to be within the scope and spirit of the invention as defined by the following claims.

What is claimed is:

1. A method for operating an endothelium reflection microscope, the apparatus comprising an optical head including: an illuminating system, for obliquely illuminating, along a side projection axis through a slit, an eyeball surface of a patient's eye; an eye-front observation optical system along a central channel in which alignment-use indicator light for positional adjustment of the imaging optical center is projected toward the eye and the resulting reflected light spot is received and imaged by a camera comprising a digital optical sensor; and an enlarged-imaging optical system arranged along a side reflection axis for enlarged observation or photographing of the subject part by the digital camera based on slit illuminating light with which the eyeball surface has been illuminated; the apparatus further comprising a drive for moving the optical head along three Cartesian directions comprising an advancement direction (Z-) generally parallel to the central channel and transverse alignment directions (X-, Y-), and a CPU controller for automatically controlling the drive, the illuminating systems, and the eye-front optical system; the method further including an alignment procedure in which the optical head is moved along the alignment directions (X-, Y-) so that the reflected light spot and the camera optical sensor are mutually centered, and an endothelium image acquisition procedure in which the optical head is moved along the advancement direction (Z-), the image acquisition procedure comprising the steps of:

(i) constantly checking the grey level inside a check area of the camera sensor, during its progression along the advancement direction (Z-), the check area being displaced generally toward a border of the sensor corresponding to the entry side of reflection of the slit light, shifting in response to movement of the optical head in the advancement direction (Z-);

(ii) when the grey level reaches a predetermined threshold value, triggering a delay time ($\Delta t$); and (iii) when the delay time ($\Delta t$) lapses, enabling acquisition of one or more images of the endothelium by the digital camera.

2. The method set forth in claim 1, wherein the check area is a strip or band extending vertically for at least a central portion of the sensor.

3. The method set forth in claim 1, wherein the grey level is checked by average calculations over all the pixels included in the check area.

4. The method set forth in claim 1, wherein the delay time ($\Delta t$) controls activation of a supplementary illuminator arranged on the side projection axis.

5. The method set forth in claim 4, wherein the supplementary illuminator includes a photo-flash, a signal for activating the same being emitted from the CPU unit to the photoflash with a selected advance relative to the lapse of the delay time ($\Delta t$).

6. The method set forth in claim 1, wherein a plurality of images of the endothelium are taken and the higher quality of the images is chosen by the operator.

7. The method set forth in claim 1, wherein the alignment procedure further comprises the steps of:

(i) continuously taking images of the reflected light spot;
(ii) on each acquired frame, identifying all the pixels in which the grey level is inside a selected range, so as to identify all the points that belong to the light spot reflected by the cornea;
(iii) evaluating the center of the light spot;
(iv) assessing the distance between the center of the light spot and the center of the sensor;
(v) changing the position of the optical head via the drive motors until the distance is below a predetermined value; and
(vi) triggering commencement of the endothelium image acquisition procedure.

8. The method set forth in claim 7, wherein the procedure is stopped or does not start if the center of the light spot is outside of a first, relatively larger control area having its center at the center of the sensor and outlined so as to discard the borders of the sensor.

9. The method set forth in claim 8, wherein the start of the endothelium image acquisition procedure is triggered when the center of the reflected light spot is inside a second, relatively smaller control area having its center at the center of the sensor.

10. The method set forth in claim 9, wherein the smaller control area comprises a pixel.

11. The method set forth in claim 7, wherein the center of the reflected light spot is evaluated by calculating the average, variance and standard deviation of the coordinates (X-, Y-) of all the pixels in the reflected light spot, with respect to a fixed reference point of the camera sensor.

* * * * *